United States Patent
Leffel

(10) Patent No.: US 9,211,394 B2
(45) Date of Patent: *Dec. 15, 2015

(54) ANGIOPLASTY BALLOON WITH CONCEAL WIRES

(75) Inventor: Kevin L. Leffel, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 385 days.

This patent is subject to a terminal disclaimer.

(21) Appl. No.: 13/247,493

(22) Filed: Sep. 28, 2011

(65) Prior Publication Data

US 2012/0022563 A1 Jan. 26, 2012

Related U.S. Application Data

(63) Continuation of application No. 12/026,461, filed on Feb. 5, 2008.

(60) Provisional application No. 60/899,802, filed on Feb. 6, 2007.

(51) Int. Cl.
*A61B 17/22* (2006.01)
*A61M 25/10* (2013.01)

(52) U.S. Cl.
CPC ..... *A61M 25/104* (2013.01); *A61M 2025/1086* (2013.01)

(58) Field of Classification Search
CPC ............... A61B 2025/1043; A61B 2025/1054; A61B 2025/1056; A61B 2025/1086; A61M 25/104
USPC .................................................. 606/159, 192
See application file for complete search history.

(56) References Cited

U.S. PATENT DOCUMENTS

| | | | |
|---|---|---|---|
| 4,406,656 A | 9/1983 | Hattler et al. |
| 4,729,763 A | 3/1988 | Henrie |
| 4,886,061 A | 12/1989 | Fischell et al. |
| 4,898,575 A | 2/1990 | Fischell et al. |
| 4,983,167 A | 1/1991 | Sahota |
| 5,019,042 A | 5/1991 | Sahota |
| 5,030,201 A | 7/1991 | Palestrant |
| 5,047,040 A | 9/1991 | Simpson et al. |
| 5,057,120 A | 10/1991 | Farcot |
| 5,078,723 A | 1/1992 | Dance et al. |
| 5,080,660 A | 1/1992 | Buelna |
| 5,090,958 A | 2/1992 | Sahota |
| 5,112,305 A | 5/1992 | Barath et al. |

(Continued)

FOREIGN PATENT DOCUMENTS

| EP | 0 117 519 | 2/1984 |
|---|---|---|
| WO | WO 2004/066852 | 8/2004 |

*Primary Examiner* — Thomas McEvoy
*Assistant Examiner* — Julie A Szpira
(74) *Attorney, Agent, or Firm* — Brinks Gilson & Lione

(57) ABSTRACT

A balloon catheter having wires situated between an outer layer and a surface of a balloon is described. Each wire may be confined within an interior space of a pocket or encapsulated within a sheath. The pocket includes the outer layer and the balloon surface. The outer layer and balloon surface are unattached to allow the wire to slidably fit between therewithin. The pocket is selectively bonded to the balloon. The sheath includes a preformed shape that completely circumscribes the wire along the longitudinal and radial directions of the wire. The confined and encapsulated feature of the wires enable the wires to be atraumatic and remain spaced apart during treatment of calcification of a lesion.

15 Claims, 11 Drawing Sheets

(56) References Cited

U.S. PATENT DOCUMENTS

| | | |
|---|---|---|
| 5,147,377 A | 9/1992 | Sahota |
| 5,160,321 A | 11/1992 | Sahota |
| 5,181,920 A | 1/1993 | Mueller |
| 5,192,291 A | 3/1993 | Pannek, Jr. |
| 5,196,024 A | 3/1993 | Barath |
| 5,209,749 A | 5/1993 | Buelna |
| 5,224,945 A | 7/1993 | Pannek, Jr. |
| 5,224,949 A | 7/1993 | Gomeinger et al. |
| 5,267,958 A * | 12/1993 | Buchbinder et al. ..... 604/103.14 |
| 5,320,605 A | 6/1994 | Sahota |
| 5,320,634 A | 6/1994 | Vigil et al. |
| 5,336,178 A | 8/1994 | Kaplin et al. |
| 5,372,601 A | 12/1994 | Lary |
| 5,395,332 A | 3/1995 | Ressemann |
| 5,409,454 A | 4/1995 | Fischell et al. |
| 5,411,478 A | 5/1995 | Stillabowerer et al. |
| 5,431,673 A | 7/1995 | Summers |
| 5,441,510 A | 8/1995 | Simpson |
| 5,505,725 A | 4/1996 | Samson |
| 5,556,408 A | 9/1996 | Farhat |
| 5,571,087 A | 11/1996 | Ressemann |
| 5,575,771 A | 11/1996 | Walinsky |
| 5,601,582 A | 2/1997 | Shelton et al. |
| 5,616,149 A | 4/1997 | Barath |
| 5,624,704 A | 4/1997 | Darouiche et al. |
| 5,628,746 A | 5/1997 | Clayman |
| 5,690,642 A | 11/1997 | Osborne et al. |
| 5,722,949 A | 3/1998 | Sanese |
| 5,728,129 A | 3/1998 | Summers |
| 5,779,698 A | 7/1998 | Clayman et al. |
| 5,792,158 A | 8/1998 | Lary |
| 5,797,935 A | 8/1998 | Barath |
| 5,814,061 A | 9/1998 | Osborne et al. |
| 5,904,679 A | 5/1999 | Clayman |
| 5,910,144 A | 6/1999 | Hayashi |
| 5,921,958 A | 7/1999 | Ressemann et al. |
| 6,033,380 A | 3/2000 | Butaric et al. |
| 6,036,689 A | 3/2000 | Tu et al. |
| 6,036,708 A | 3/2000 | Sciver |
| 6,042,590 A * | 3/2000 | Sporri et al. .................. 606/135 |
| 6,071,285 A | 6/2000 | Lashinski et al. |
| 6,123,718 A | 9/2000 | Tu et al. |
| 6,165,187 A | 12/2000 | Reger |
| 6,231,572 B1 | 5/2001 | Hart et al. |
| 6,245,040 B1 | 6/2001 | Inderbitzen et al. |
| 6,280,464 B1 | 8/2001 | Hauashi |
| 6,283,947 B1 | 9/2001 | Mirzaee |
| 6,306,151 B1 | 10/2001 | Lary |
| 6,355,013 B1 | 3/2002 | Van Muiden |
| 6,371,961 B1 | 4/2002 | Osborne et al. |
| 6,500,186 B2 | 12/2002 | Lafontaine et al. |
| 6,632,231 B2 | 10/2003 | Radisch |
| 6,746,463 B1 | 6/2004 | Schwartz |
| 6,808,531 B2 | 10/2004 | Lafontaine et al. |
| 6,855,124 B1 | 2/2005 | Gonzalez |
| 7,258,696 B2 * | 8/2007 | Rabkin et al. ................ 623/1.11 |
| 7,566,319 B2 * | 7/2009 | McAuley et al. ........ 604/103.08 |
| 7,708,753 B2 * | 5/2010 | Hardert ........................ 606/192 |
| 2002/0035389 A1 * | 3/2002 | Richter et al. ................ 623/1.11 |
| 2003/0028212 A1 * | 2/2003 | Saab ............................ 606/192 |
| 2003/0114877 A1 | 6/2003 | Gellman |
| 2004/0073297 A1 | 4/2004 | Rohde et al. |
| 2004/0122465 A1 | 6/2004 | McMurtry et al. |
| 2004/0143286 A1 * | 7/2004 | Johnson et al. ................ 606/194 |
| 2004/0143287 A1 | 7/2004 | Konstantino et al. |
| 2004/0193196 A1 | 9/2004 | Appling et al. |
| 2004/0199191 A1 | 10/2004 | Schwartz |
| 2005/0021070 A1 | 1/2005 | Feld et al. |
| 2005/0021071 A1 | 1/2005 | Konstantino et al. |
| 2005/0149082 A1 * | 7/2005 | Yee et al. ...................... 606/159 |
| 2005/0288629 A1 | 12/2005 | Kunis |
| 2006/0111736 A1 | 5/2006 | Kelley |
| 2006/0173487 A1 | 8/2006 | Uflacker et al. |
| 2007/0027524 A1 * | 2/2007 | Johnson et al. ................ 623/1.11 |
| 2007/0073329 A1 | 3/2007 | Hardert |
| 2007/0106215 A1 | 5/2007 | Olsen |
| 2007/0118200 A1 * | 5/2007 | Weber et al. .................. 623/1.11 |
| 2008/0039787 A1 * | 2/2008 | McMurtry et al. ........ 604/103.03 |
| 2008/0147103 A1 * | 6/2008 | Shekalim ...................... 606/159 |

\* cited by examiner

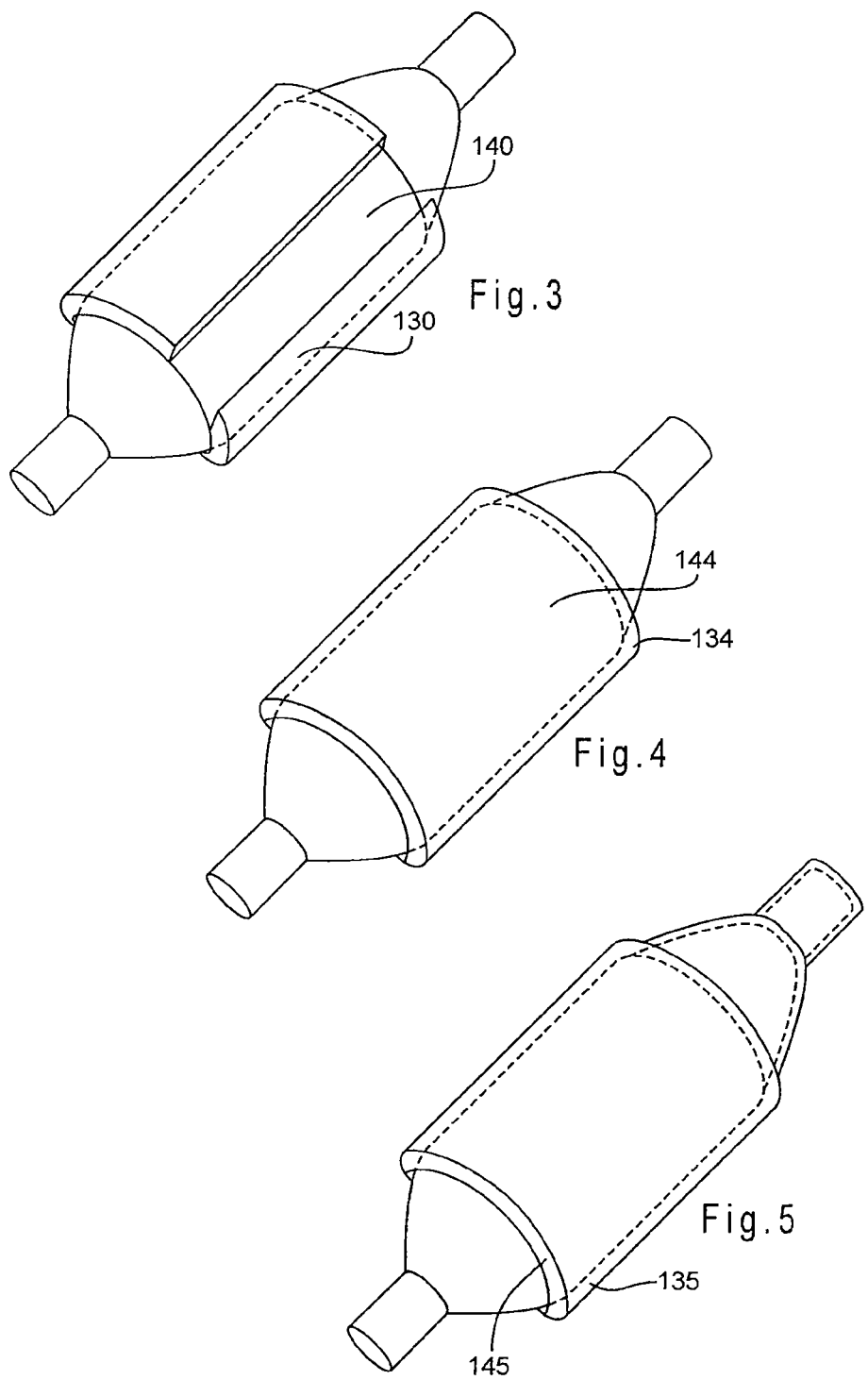

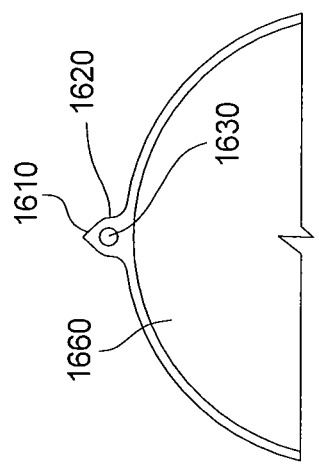
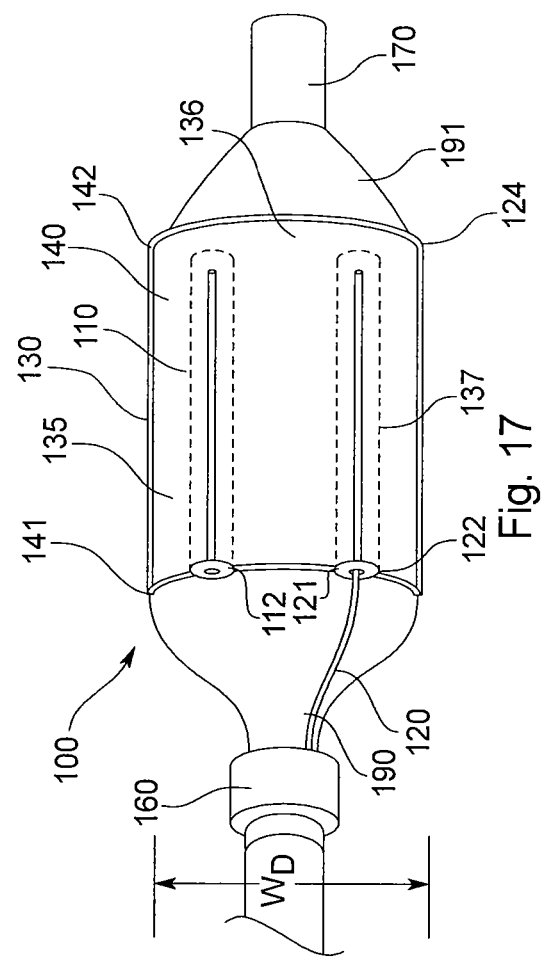

ANGIOPLASTY BALLOON WITH CONCEAL WIRES

RELATED APPLICATIONS

This application claims the benefit under 35 U.S.C. §120 as a continuation of U.S. patent application Ser. No. 12/026,461, filed Feb. 5, 2008, and claims the benefit under 35 U.S.C. §119(e) of U.S. Provisional Application No. 60/899,802, filed Feb. 6, 2007, both of which are hereby incorporated by reference herein.

TECHNICAL FIELD

The present invention relates generally to medical devices and more particularly to balloon catheters used to dilate narrowed portions of a lumen.

BACKGROUND

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. This has lead to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. Although the inventions described below may be useful in treating hardened regions of a stenosis, the claimed inventions may also solve other problems as well.

SUMMARY

Accordingly, a balloon catheter is provided in which a wire is situated within a pocket or a sheath.

The invention may include any of the following aspects in various combinations and may also include any other aspect described below in the written description or in the attached drawings.

A balloon catheter for dilation of a body lumen, comprising: a shaft having a distal end and a proximal end; a balloon mounted on the distal end of the shaft, the balloon having a distal portion and a proximal portion, the shaft having an inflation lumen extending therethrough in fluid communication with an interior region of the balloon, the balloon thereby being expandable between a deflated state and an inflated state; and a wire extending along an outer surface of the balloon, the wire disposed between the outer surface of the balloon and an outer layer, the outer layer at least partially circumscribing the wire along a longitudinal length of the wire, the outer layer having an axial length, the outer layer being attached to the outer surface of the balloon at one or more locations.

The balloon catheter, wherein the outer layer is unattached to the outer surface of the balloon at one or more predetermined regions, the unattachment forming a pocket between the outer layer and the outer surface of the balloon for the wire to be disposed therewithin.

The balloon catheter, wherein the pocket is longitudinally aligned with a longitudinal axis of the balloon, the pocket comprising a first opening adapted to slidably receive a wire.

The balloon catheter, the pocket further comprising a seam to define the edges of the pocket.

The balloon catheter, wherein a retaining element is affixed to the wire to maintain the wire in the pockets.

The balloon catheter, wherein the first end is sealed to enclose the wire within the pocket.

The balloon catheter, wherein the wire is not bonded to interior surfaces of the pocket.

The balloon catheter, wherein the outer layer encapsulates the wire, the outer layer completely circumscribing the wire along the longitudinal length of the wire.

The balloon catheter, wherein the outer layer is a polymeric sheath.

A balloon catheter for dilation of a body lumen, comprising: a shaft having a distal end and a proximal end; a balloon mounted on the distal end of the shaft, the shaft having an inflation lumen extending therethrough in fluid communication with an interior region of the balloon, the balloon thereby being expandable between a deflated state and an inflated state, wherein at least a length of an outer surface of the balloon comprises a working diameter adapted to dilate the body lumen, the length extending between a balloon proximal end and a balloon distal end; a pocket situated along the outer surface of the balloon, the pocket comprising an interior space defined by portions of an outer layer selectively unattached to the outer surface, the pocket further comprising a seam defined by portions of the outer layer attached to the outer surface of the balloon, the outer layer disposed over the outer surface of the balloon and extending along the working diameter of the balloon; a wire residing within the pocket; and a retaining element affixed to the wire, the retaining element preventing the wire from sliding out of the pocket.

The balloon catheter, the seam comprising an undulating shape.

The balloon catheter, wherein the attachment of the outer layer to the outer surface of the balloon at the one or more locations comprises bonding the outer layer to the outer surface.

The balloon catheter, wherein the bonding comprises heat bonding, solvent bonding, or adhesive bonding.

The balloon catheter, wherein the catheter comprises a plurality of pockets.

The balloon catheter, wherein the plurality of pockets are longitudinally aligned with a longitudinal axis of the balloon, the plurality of pockets being circumferentially equidistant from each other.

A balloon catheter for dilation of a body lumen, comprising: a shaft having a distal end and a proximal end; a balloon mounted on the distal end of the shaft, the shaft having an inflation lumen extending therethrough in fluid communication with an interior region of the balloon, the balloon thereby being expandable between a deflated state and an inflated state, wherein at least a length of an outer surface of the balloon comprises a working diameter adapted to dilate the body lumen, the length extending between a balloon proximal end and a balloon distal end; and a wire comprising an axial length, the wire encapsulated by a sheath situated along the working diameter of the balloon, the sheath circumscribing the wire along the entire axial length of the wire, the sheath disposed over an outer surface of the balloon.

The balloon catheter, the sheath having a tubular shape, the sheath fusion bonded to the outer surface of the balloon.

The balloon catheter, the sheath movable between a first position and a second position, wherein the first position comprises a resting state where the balloon is deflated and the second position comprises a stretched state where the balloon is inflated.

The balloon catheter, the wire comprising a non-adhesive coating to minimize bonding with the sheath.

The balloon catheter, the sheath comprising a cutting edge.

The balloon catheter, the wire having a proximal end and a distal end, the sheath axially extending past the proximal and the distal ends.

BRIEF DESCRIPTION OF THE DRAWINGS

Embodiments will now be described by way of example with reference to the accompanying drawings, in which:

FIG. 3 is perspective view of a balloon catheter having an outer layer in the form of a sheet wrapped around the outer surface of the balloon;

FIG. 4 is a perspective view of a balloon catheter having an outer sleeve disposed about a balloon;

FIG. 5 is a perspective view of an outer balloon portion slid over an underlying balloon;

FIG. 16 is a cross-sectional view of a balloon attached to a sheath, the sheath having a cutting edge and encapsulating a wire therewithin;

FIG. 17 is a perspective view of a balloon catheter with one wire disposed within a pocket and another wire secured to a retaining element.

DETAILED DESCRIPTION OF THE PREFERRED EMBODIMENTS

Figure 1:
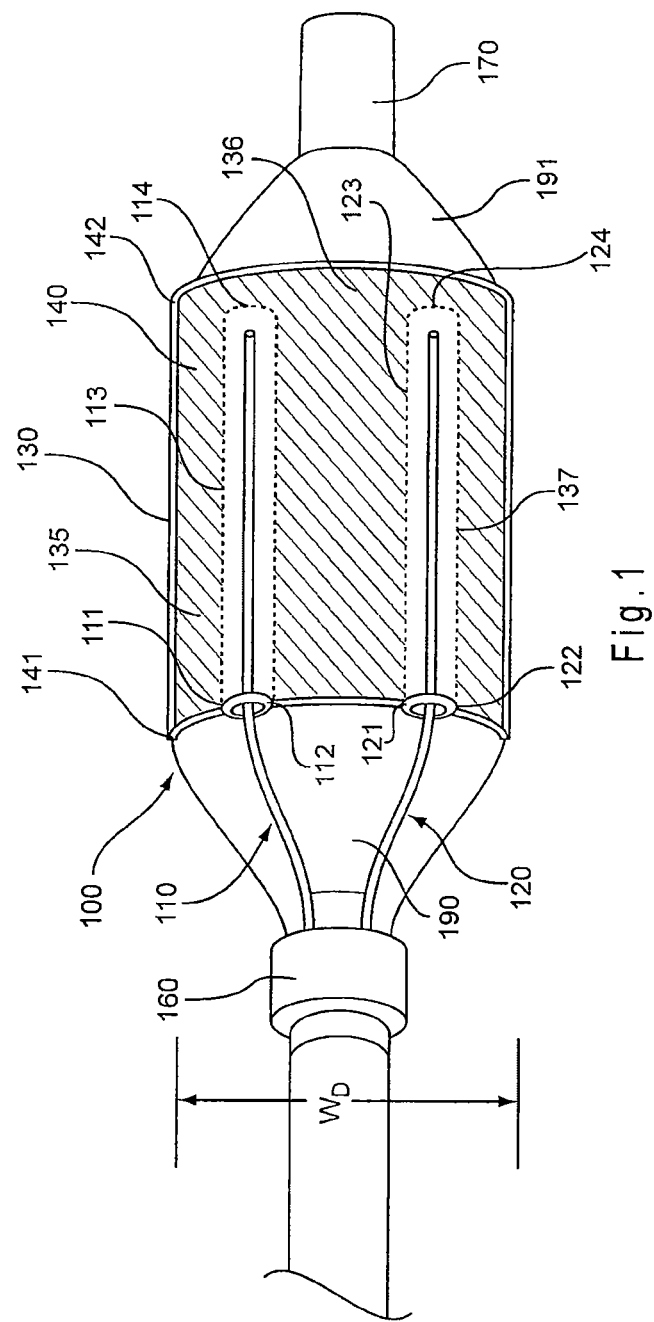
FIG. 1 is a perspective view of a balloon catheter with wires disposed within pockets.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Referring now to the drawings in FIGS. 1-18, a balloon catheter with wires is shown. As will be discussed, the wires may be disposed within a sheath or a pocket. The wires may be wrapped into the folds of the balloon. However, for purposes of clarity, the Figures do not show such a pleated configuration to enable illustration of the wires within their pockets and connection of the wires to the balloon and shaft.

FIG. 1 shows an exemplary balloon catheter 100 having wires 110 and 120 disposed within pockets 111 and 121, respectively. The balloon catheter 100 includes a shaft 170 and a balloon 140. The catheter shaft 170, as shown in FIG. 1, may have a diameter ranging between about 3 FR and about 12 FR. Preferably, the shaft 170 has a diameter of about 7 FR.

The balloon 140 is shown in its inflated state. An outer surface of the balloon 140 has a working diameter, denoted as $W_D$, which extends along a part of the length of the balloon 140. Typically, the working diameter of the balloon 140 is a portion that inflates to a generally uniform circumference in order to evenly dilate a section of a lumen. However, the working diameter does not necessarily need to have a uniform circumference. The working diameter of the balloon 140 may be connected to the shaft 170 with a tapered proximal portion 190 and a tapered distal portion 191. The length of the working diameter may be defined as the distance between the balloon proximal end 141, where the tapered proximal portion 190 meets the working diameter, and the balloon distal end 142, where the tapered distal portion 191 meets the working diameter.

Still referring to FIG. 1, the pocket 111 has an opening 112 through which the wire 110 may be inserted. The wire 110 extends within the pocket 111. Similarly, the pocket 121 has an opening 122 through which wire 120 may be inserted. The wire 120 extends within the pocket 121. Pockets 111, 121 have interior spaces for the respective wires 110, 120 to be disposed within. Pocket 111 has a continuous seam 113 that may constrain the wire 110 within the interior space. The seam 113 represents the locations where an outer layer 130 is disposed over and bonded to the outer surface of the balloon 140. The distal end 114 of the seam 113 may be sealed off, thereby preventing the wire 110 from extending therethrough. Pocket 121 also has a continuous seam 123 that constrains the wire 120 within the interior space. The seam 123 represents the locations where the outer layer 130 is disposed over and affixed to the outer surface of the balloon 140. The distal end 124 of the seam 123 is sealed off, thereby preventing the wire 120 from extending therethrough. Regions 135, 136 and 137 represent locations where the outer layer 130 has been bonded to the outer surface of the balloon 140. The outer layer 130 may be bonded to the outer surface of the balloon 140 by a variety of ways known to one of ordinary skill in the art, including heat bonding, adhesive bonding, or solvent bonding. These types of bonding will be explained in greater detail below.

A retaining element 160 may secure wire 110 and/or wire 120 in position. The retaining element 160 prevents wires 110, 120 from sliding out of their respective pockets 111, 121. Because the proximal hub is where the largest diameter of the balloon catheter 100 resides, it is preferable to have the retaining element 160 located on the proximal hub of the balloon 140, as shown in FIG. 1.

Figure 18:
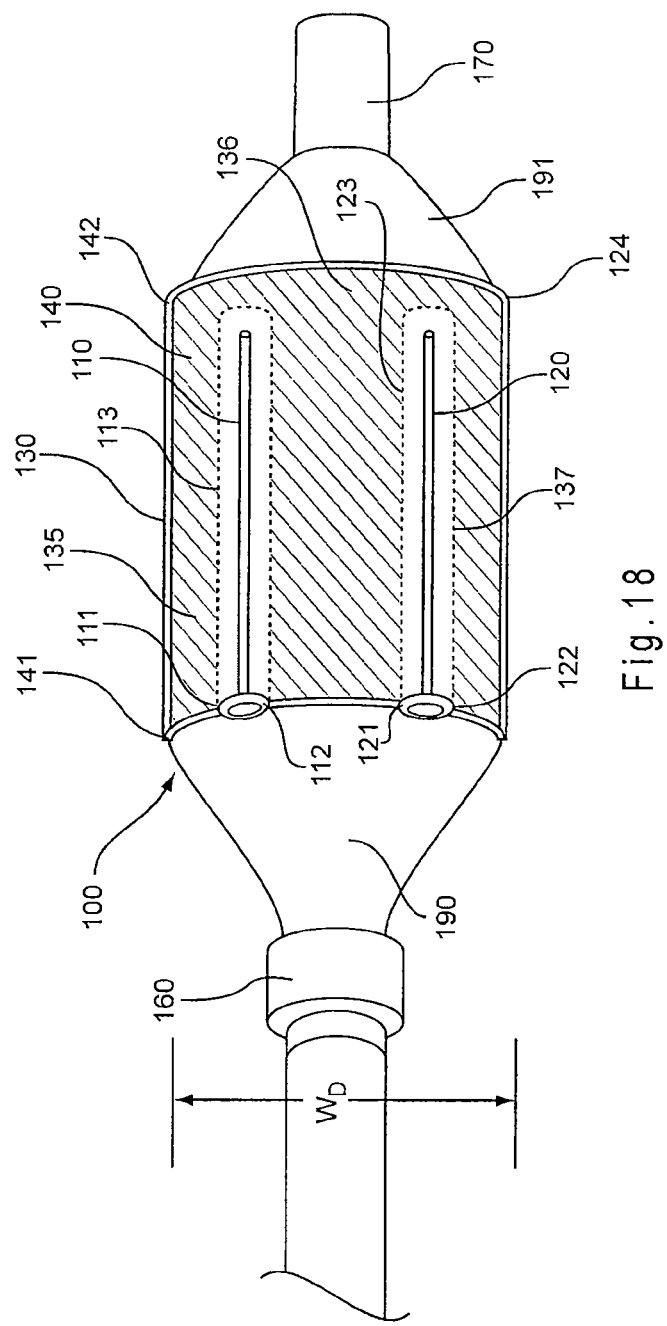
FIG. 18 is a perspective view of a balloon catheter with two wires each disposed within their respective pockets.

Alternatively, the wires 110 and 120 may be loosely disposed within their respective pockets 111 and 121, as shown in FIG. 18. The wires 110 and 120 are not attached to the retaining element 160. FIG. 18 shows that the opening 112 of pocket 111 and opening 122 of pocket 121 may be sealed off to enclose the wires 110, 120 within the interior regions of the pockets 111, 121. The seal may include a suture or adhesive. Other ways of sealing the openings 112, 122 of the pockets 111, 121 are contemplated and may be obvious to one of ordinary skill in the art.

FIG. 17 shows yet another type of balloon catheter in which one of the wires is loosely disposed within a pocket and the other wire is attached to a retaining element. Specifically wire 110 is loosely disposed within pocket 111, and the proximal end of wire 120 extends from pocket 121 and attaches to retaining element 160.

Referring back to FIG. 1, although two wires are shown disposed within their respective pockets, more than two wires may be disposed within a single pocket. Preferably, each wire resides in its own pocket. Additionally, although the wires 110, 120 are shown extending parallel to the longitudinal axis of the balloon, the wires 110, 120 may be configured in a non-parallel arrangement such as a helical arrangement around the working diameter of the balloon 140.

The composite thickness of the balloon 140 and outer layer 130 remain relatively thin such that they can be folded in the conventional pleated arrangement during delivery to achieve a small profile. Preferably, the outer layer 130 does not provide a hindrance to the folding or pleating process.

Figure 2A:
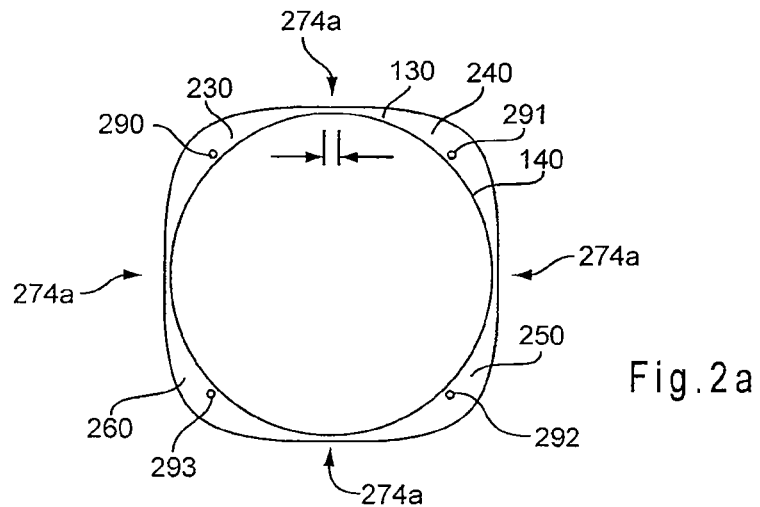
FIGS. 2a-2c are cross-sectional views of balloon catheters with wires disposed within pockets of various geometries.
Figure 2B:
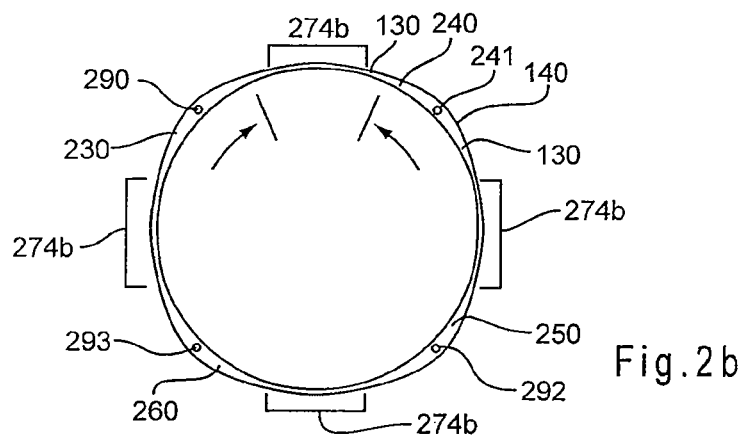
Figure 2C:
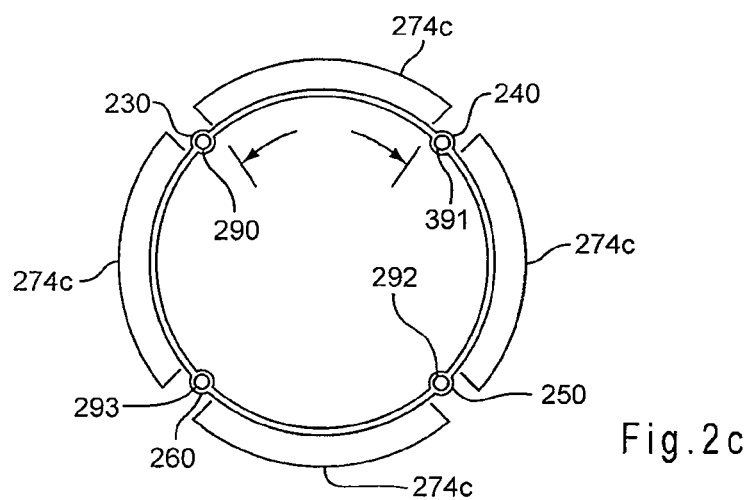

Various types of pocket configurations are contemplated. FIGS. 2a-2c show examples of different pocket geometries. FIG. 2a shows a configuration in which the outer layer 130 is selectively attached to various locations around the balloon 140. The outer layer 130 is unattached to the balloon along four locations to produce pockets 230, 240, 250, 260. The points of attachment 274a of the outer layer 130 to the balloon are relatively low-contact area bonds. The low-contact area bonds allow the width of the pockets 230, 240, 250, 260 to be greater than the diameter of their respective wires 290, 291, 292, 293 disposed therewithin, thereby providing the wires 290, 291, 292, 293 free space to move within the interior regions of the pockets 230, 240, 250, 260. The free space surrounding each of the wires 290, 291, 292, 293 within the interior regions of their respective pockets 230, 240, 250, 260 may allow the wires 290, 291, 292, 293 to flex during navigation of the balloon catheter through tortuous regions. The ability of the wires 290, 291, 292, 293 to flex may help maintain the wires 290, 291, 292, 293 on the balloon 140 (FIG. 1) without a high risk of tearing from the surface of the balloon 140. Additionally, the free space surrounding each of the wires 290, 291, 292, 293 within their respective pockets 230, 240, 250, 260 enables any longitudinal movement that the pockets 230, 240, 250, 260 may undergo upon inflation of the balloon 140 without undue stress on the wires 290, 291, 292, 293.

FIG. 2b shows a configuration in which the outer layer 130 is selectively attached to various locations around the balloon 140. The regions of attachment 274b of the outer layer 130 to the balloon 140 can be characterized as intermediate-contact area bonds relative to the contact areas shown in FIG. 2a. The outer layer 130 is unattached to the balloon 140 along four locations to produce pockets 230, 240, 250, 260 in which respective wires 290, 291, 292, 293 are disposed therewithin. The intermediate-contact area bonds cause the pockets 230, 240, 250, 260 to be smaller than the pockets illustrated in FIG. 2a.

FIG. 2c shows a configuration in which the regions of attachment 274c of the outer layer 130 to the balloon 140 can be characterized as high contact-area bonds relative to the contact areas shown in FIGS. 2a and 2b. The high contact-area bonds produce pockets 230, 240, 250, 260 in which respective wires 290, 291, 292, 293 are disposed therewithin. The high-contact area bonds cause the pockets 230, 240, 250, 260 to be smaller than the pockets illustrated in FIGS. 2a and 2b.

There are various ways to apply the outer layer 130 to the outer surface of the balloon 140, as shown in FIGS. 3-5. For example, FIG. 3 shows that the outer layer 130 may be a sheet that can be wrapped around the outer surface of the balloon 140. Alternatively, FIG. 4 shows that the outer layer 134 may be a cylindrical sleeve wrapped around the outer surface of the balloon 144. FIG. 5 shows that the outer layer 135 is formed from another portion of a balloon in which one end of it has been removed and slid over the underlying balloon 145. Preferably, the outer balloon 135 is slid over the underlying balloon 145 with the underlying balloon 145 in its deflated state to create an intimate fit between the two balloons 135 and 145. After achieving the fit, the balloons 135 and 145 may be partially inflated and thereafter bonded to one another via heat bonding, adhesive bonding, or solvent bonding. The outer layer 135 may be surface treated (e.g., roughened) in order to improve the adhesion at the bond sites between the balloon 145 and the outer layer 135. As FIG. 5 shows, the outer layer 135 may span beyond the working diameter of the underlying balloon 145 to facilitate handling or sealing. Other ways of attaching the outer layer 135 to the underlying balloon 145 are contemplated and may be obvious to one of ordinary skill in the art.

Figure 6:
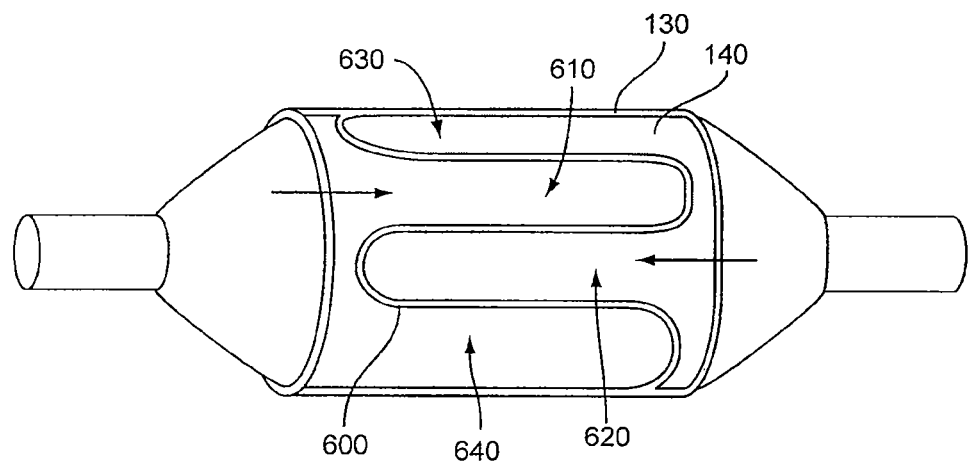
FIG. 6 is a perspective view of an outer layer bonded to a balloon to form pockets.

After the outer layer 130 has been attached to the balloon 140 (FIG. 3), the pockets may be formed. FIG. 6 is an example of selectively heat bonding or laser bonding the outer layer 130 at predetermined regions to the balloon 140. In particular, FIG. 6 shows the result of heat bonding or laser bonding the outer layer 130 to the balloon 140 to form a continuous seam 600. In other words, the seam 600 represents the points that the outer layer 130 is bonded to the balloon 140. The seam 600 has a serpentine configuration which extends around the circumference of the working diameter of the balloon 140. Because the outer layer 130 is only attached to the balloon 140 at the seam 600, pockets 610, 620, 630, 640 are formed proximal and distal to the undulating seam 600. In other words, the pockets are accessible from both the distal end and proximal end of the balloon 140. Because the seam 600 symmetrically extends around the circumference of the balloon 140, there are also four pockets on the opposite 180° of the balloon 140, which are not shown. All eight of the pockets are equally spaced apart. One wire may be slidably disposed into each pocket. For example, one wire may slide along the distal direction into pocket 610, as indicated by the arrow pointing into pocket 610, while another wire may slide along the proximal direction into pocket 620, as indicated by the arrow pointing into pocket 620.

Because the balloon 140 will be movable from a deflated state to an inflated state, the wires may have a tendency to slide out of the pocket 610, 620, 630, 640 and/or the pockets 610, 620, 630, 640 may have a tendency to longitudinally move relative to the wires. Consequently, a retaining element 160 such as a collar (FIG. 1), may be fastened to the wires to maintain the positioning of the wires in their respective pockets 610, 620, 630, 640. Alternatively, the openings of the pockets 610, 620, 630, 640 that the wires slide into may be sealed to confine the wire within the pockets 610, 620, 630, 640. As an example, the openings may be sutured, heat bonded, or sealed with an adhesive. If the openings of the pockets 610, 620, 630, 640 are sealed, then the individual wires preferably have an axial length approximating the axial length of the pockets 610, 620, 630, 640.

Nonetheless, it may be preferable to allow the wires to move within the pockets to enable them to flex and bend. This feature may be advantageous, for example, as the balloon is being navigated through tortuous body lumens. Thus, a non-adhesive coating, which is also known as a release agent, may be applied to one or more surfaces of the wires to prevent the wires from adhering to the inner surfaces of the pockets 610, 620, 630, 640.

Although the seam 600 has been shown to be a serpentine-configured heat bonded or laser bonded line, other shapes of the seam 600 are possible. The shape of the seam 600 may determine the geometry of the pockets 610, 620, 630, 640 that the wires are inserted into.

Figure 7:
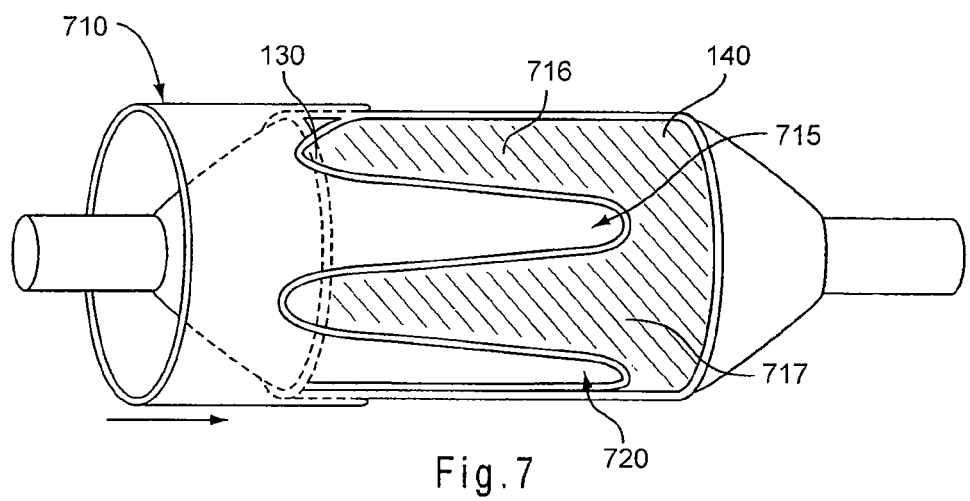
FIG. 7 is a perspective view of a mechanical mask disposed over the balloon as the outer layer is bonded to the balloon.

FIG. 7 shows another way that pockets may be formed. A removable mechanical mask 710 is shown overlying an outer surface of the balloon 140. The mask 710 may be formed from a variety of materials such as Teflon. The mask 710 may have a fingerlike-like structure. The mask 710 acts to block bonding between the outer surface of the balloon 140 and the outer layer 130. FIG. 7 shows the mask 710 positioned over the balloon 140. With the mask 710 positioned over the balloon 140, as shown by the arrow in FIG. 7, a light sensitive adhesive may be applied to the outer layer 130 or both the outer layer 130 and the outer surface of the balloon 140 along regions 716 and 717. In other words, adhesive is applied to bond those areas of the balloon 140 with the outer layer 130 that are not covered by the mechanical mask 710. Any adhesive known to one of ordinary skill in the art may be used. After the adhesive has cured such that the bond has stabilized, the mask 710 may be removed. As shown, the fingers of the mask 710 may be designed to be tapered or inclined relative to the surface of the balloon 140 so that the mask 710 may be relatively easy to withdraw after the adhesive has cured over regions 716 and 717. The proximal end of the mask 710 may extend past the proximal end of the balloon 140, as shown in FIG. 7, for easy handling of the mask 710. Masked regions 715 and 720 may correspond to the interior space of the newly formed pockets 715 and 720. The locations at which the balloon 140 bonds to the outer layer 130 form the seam of pockets 715 and 720. Two additional pockets may also be formed on the other side of the balloon 130 to create a total of four pockets. As an alternative to a mechanical mask 710, a chemical mask may be utilized. Any type of chemical mask known to one of ordinary skill in the art may be used, including oils and lubricants. Removal of the chemical mask may involve chemically rinsing with an inert chemical that may not react with the outer layer 130, which is now bonded to the outer surface of the balloon 140. Because there is no chemical interaction between the layers when adhesive bonding is used, the outer layer 130 may be formed from a material dissimilar from the balloon 140.

Larger pockets of FIGS. 6 and 7 as compared to FIG. 8 might be advantageous when negotiating tortuosity and making sure that the wires rest in their intended positions during folding operations.

Referring back to FIG. 1, the pockets may be created utilizing a chemical process known as solvent bonding. Unlike the methods of forming pockets discussed in FIGS. 6 and 7, the pockets of FIG. 1 may be created directly around the wires. The pockets 111, 121 that are created in FIG. 1 have a smaller interior space relative to the pockets shown in FIGS. 6 and 7. The pockets 111, 121 of FIG. 1 may be created as follows. The wires 110 and 120 of FIG. 1 are held in their desired position along the balloon 140 before the pockets 111, 121 are formed around the wires 110, 120. With the wires 110 and 120 selectively positioned along the balloon 140, the outer layer 130 is solvent bonded to the balloon 140. Solvent bonding involves the following. A solvent is applied to the outer layer 130 and balloon 140. A suitable solvent is selected that causes both the outer layer 130 and the balloon 140 to partially dissolve with the solvent. The dissolution of the outer layer 130 and the balloon 140 causes liquefaction along regions 135, 136 and 137. The solvent may evaporate at ambient temperature or can be driven off with heat. When the solvent evaporates, the outer layer 130 and the balloon 140 will re-solidify. As they re-solidify, the outer layer 130 and balloon 140 become bonded. Pressure may be applied to the outer layer 130 and balloon 140 to hold them together as the solvent evaporates. Any type of solvent known to one of ordinary skill in the art may be used, including acetone, toluene, methylene chloride, and methyl ethyl ketone.

In the solvent bonding method, a mask may not be required as the wires 110, 120 may prevent the outer layer 130 from solvent bonding to the balloon 140 within the local area where the wires 110, 120 reside. Alternatively, a release agent or surface treatment may be applied to the wires 110, 120 to further prevent any tendency the wires 110, 120 may have to adhere to the outer layer 130.

Note that in all of the examples of pocket formation discussed, the balloon 140 is preferably at least semi-inflated when the outer layer 130 is bonded to the balloon 140. Applying the outer layer 130 to at least a semi-inflated balloon 140 may enable greater control of where the bonds are formed.

Figure 8A:
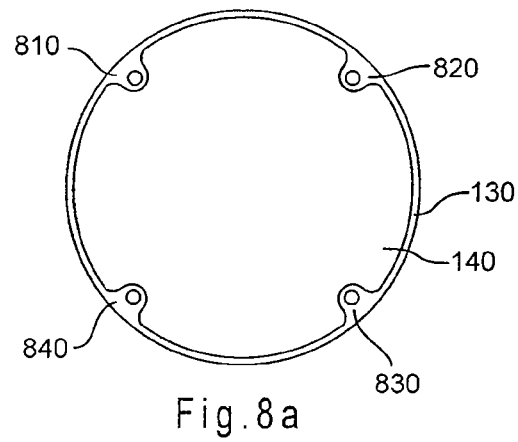
FIGS. 8a-8c are cross-sectional views of balloon catheters with wires disposed within pockets produced by inward, neutral and outward biasing, respectively.
Figure 8B:
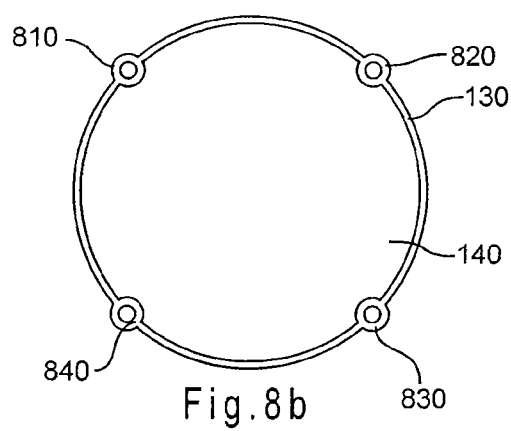
Figure 8C:
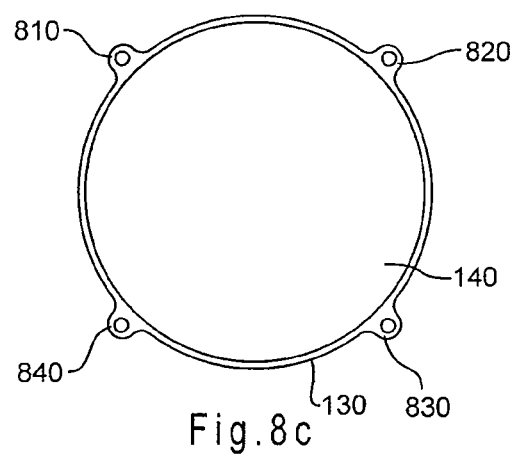

FIGS. 8a-8c illustrate the concept of biasing. The term "biasing" as used herein refers to whether the pockets protrude radially inward or radially outward relative to the surface of the balloon. As an example, the pocket configuration shown in FIG. 2c may be modified to produce the pocket arrangements shown in FIGS. 8a-8c. Generally speaking, the extent to which a bias is created may be determined by the net pressure exerted by the balloon and the net pressure exerted on the balloon as the outer layer is added over the surface of the balloon.

FIG. 8a shows pockets 810, 820, 830, 840 having an inward bias. The inward bias is created by a controlled balance of various fabrication factors, including the tension of any mask being utilized, the inflation pressure of the balloon 140, and the tightness of the outer layer 130 over the balloon 140. Creation of an inward bias results from the net pressure on the balloon 140 being greater than the net pressure exerted by the balloon 140. FIG. 8b shows pockets 810, 820, 830, 840 that have a neutral bias in which the net pressure exerted against the balloon 140 is exactly offset by the net pressure exerted by the balloon 140. FIG. 8c shows pockets 810, 820, 830, 840 that have an outward bias in which the net pressure exerted against the balloon 140 is greater than the net pressure exerted on the balloon 140.

Selecting an inward, outward, or neutral bias will depend on numerous factors, including the target site that the balloon catheter is to be delivered to and the desired delivery profile of the balloon catheter as it navigates through tortuous vessels.

Figure 9A:
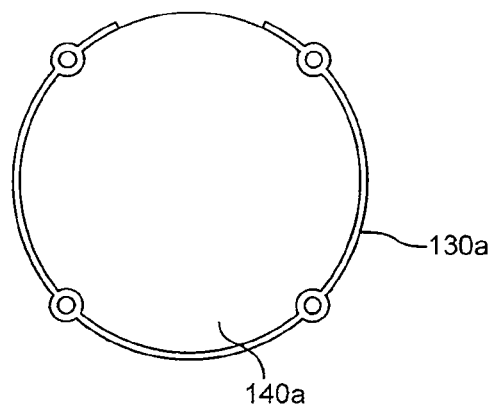
FIGS. 9a-9c are cross-sectional views of examples of the various configurations of the outer layer disposed over the balloon.
Figure 9B:
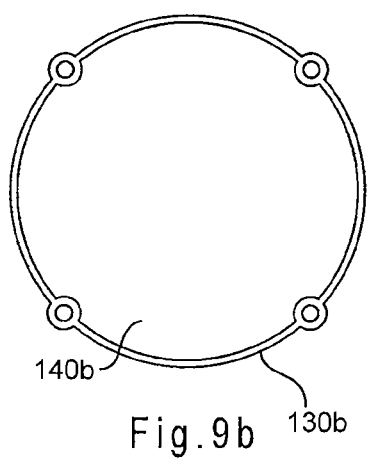
Figure 9C:
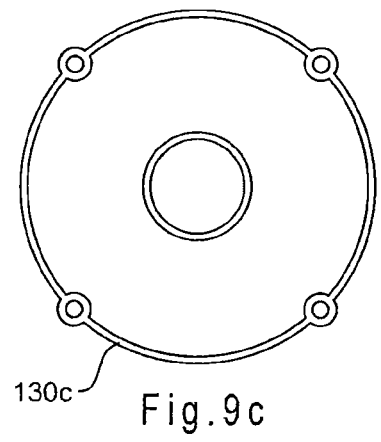

FIGS. 9a-9c show examples of the various configurations of the outer layer and types of outer layers that are contemplated. FIG. 9a illustrates an outer layer 130a that partially circumscribes the wires to form the required pockets. The outer layer 130a may be a ribbon, coating or covering. However, the outer layer 130a does not wrap completely around the balloon 140a. Such a configuration may be advantageous from a manufacturing standpoint. FIG. 9b illustrates that the outer layer 130b may be a continuous tubular sleeve that coaxially slides over the balloon 140b. FIG. 9c shows an outer balloon portion forming the outer layer 130c.

In all of the various examples that have been discussed, it is desirable for the wires to not adhere to any of the inside surfaces of the pockets. Having an unattached wire confined within a pocket enables longitudinal compliance of the wire in which the wire may readily conform to the changes in shape that the pocket undergoes as the balloon 140 moves from a relatively flat deflated state to a relatively cylindrical inflated state. Additionally, an unattached wire may readily flex when the balloon is being navigated through tortuous body lumens, thereby reducing the risk that a tightly attached wire may be torn from the surface of the balloon 140.

Utilizing a balloon catheter in which the wire is confined within a pocket may offer numerous advantages over a balloon catheter in which the wire is exposed. Because the wire is contained within two layers, it is naturally shielded from tissue and therefore cannot inadvertently catch on tissue or damage healthy tissue. These advantages reduce the need to undergo normal balloon folding operations in which pleats are created within the balloon. Thus, the wires are significantly more atraumatic as compared to wires that remain exposed over the balloon surface.

Furthermore, having wires that are confined in their respective pockets allow the wires to remain spaced apart at their predetermined gaps during fracturing of calcified lesions. On the other hand, balloon catheters with exposed wires which are affixed at one or both ends of the shaft may have a tendency to move relative to one another during inflation of the balloon, thereby making control of the relative location of the wires more difficult. As a result of the inadvertent movement, the wires may move to an undesired location on the balloon catheter that fails to contact a calcified lesion. Additionally, because calcified lesions can be asymmetric being built-up on only side of the wall of a body lumen, when a balloon catheter with exposed wires encounters a calcified lesion, there may be a tendency for the balloon to inflate towards a particular side of the body lumen. Thus, exposed wires may have a tendency to move toward a particular side that fails to contact the lesion. Furthermore, spinning of the balloon may cause exposed wires to inadvertently catch on tissue, thereby not allowing the wires to move with the balloon to the desired lesion. Therefore, wires that are confined and can only move within the interior space of the pockets may significantly reduce the risk of inadvertent movement of the wires.

Referring to the structure of FIG. 1, the positioning of the wires 111, 121 about the circumference of the balloon 140 may generally be determined by the geometry of the stenosis. For example, if an asymmetric stenosis is being treated, a greater number of the wires may be positioned adjacent to the thickest part of the stenosis.

One or more wires may be selectively positioned about the balloon. The optimal number of dilation wires may vary depending on the severity and type of stenosis to be dilated. Preferably, the number of wires will be at least two and the wires will be equidistant from each other.

Various shapes of the wires may be used. Differing wire shapes enable the force that is concentrated on the vessel wall to be varied as desired. For instance, a D-shaped cross-sectional wire may in certain applications be preferable over a circular-shaped cross-sectional wire. The D-shaped cross-sectional wire may increase the area of the wire in contact with the balloon, relative to the area of the circular-shaped wire in contact with the balloon. The D-shaped wire may also minimize the area that contacts the vessel, relative to the area of the circular-shaped wire in contact with the vessel. Accordingly, a higher stress may be exerted against the vessel wall by the D-shaped wire relative to the circular-shaped wire. As another example, a V-shaped cross-sectional wire may also be used.

If a substantially round cross-sectional configuration for the dilation wires is used, the diameters may vary depending on the particular blood vessel in which the stenosis is found and the size of the remaining lumen within the blood vessel. For round wires, a diameter of about 0.25 mm to about 5 mm is generally preferred.

Although longitudinally extending wires have been described, the wires may also be formed to have other shapes in their relaxed state. For example, the wires may be helixes that wrap around the balloon. Other shapes are also possible. Such configurations of the wires may be preferable for the purpose of minimizing the profile of the balloon catheter during delivery to a target site as well as fracturing plaques having a tortuous geometry around a blood vessel.

Figure 10:
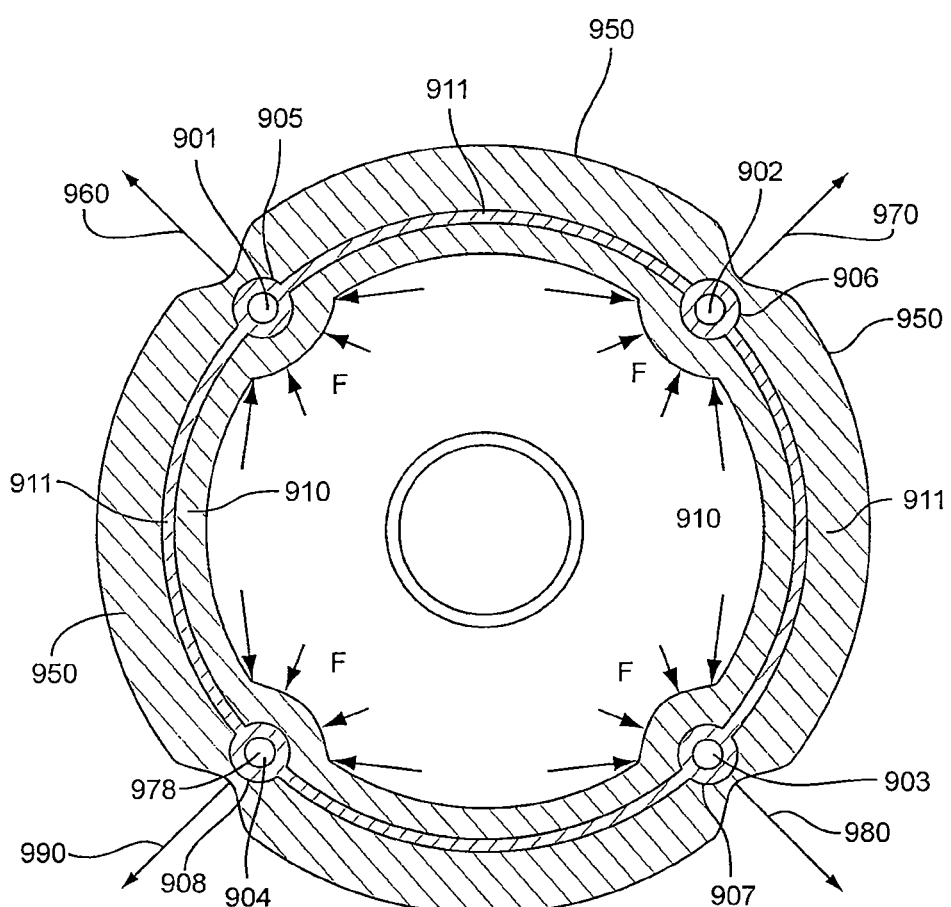
FIG. 10 is a cross-sectional view of a balloon catheter showing the concentration of force through each of four wires that are disposed within their respective pockets.

The dilation mechanism will now be described. FIG. 10 is a partial cross-sectional view of a balloon catheter taken along a plane that is distal to the inflation lumen of a balloon 910. FIG. 10 shows the balloon 910 in an inflated state. Generally speaking, the dilation mechanism involves a technique in which the forces resulting from inflating an angioplasty balloon in a stenosis are concentrated and focused at one or more locations within the stenosis. While the technique has been shown to be useful in resolving resistant stenoses, it may also minimize the vascular trauma associated with balloon angioplasty and subsequently improve the outcome.

Referring to FIG. 10, the pockets 905-908, in which the dilation wires 901, 902, 903, 904 reside, resist complete expansion of the balloon 910 at the balloon-pocket interfaces. As a result of the resistance, the balloon 910 does not reach its fully inflated circumference. The balloon-pocket interfaces are shown as recessed due to the resistance of the pockets 905-908 against the surface of the inflated balloon 910.

The balloon 910 may radially expand to the circumference shown in FIG. 10. The inflation pressure causes the balloon 910 to exert a force against each of the pockets 905-908. The force exerted at each of the balloon-pocket interfaces is designated as F in FIG. 10. This causes the pockets 905-908 to push out toward the vessel wall 950.

The dilation wires 901, 902, 903, 904, which are positioned between the outer layer 911 and the balloon 910, focus the force, F, of the balloon 910 at their respective points of contact of the pockets 905, 906, 907, 908 with the vessel wall 950, as shown by arrows 960, 970, 980 and 990 of FIG. 10. Additionally, the dilation wires 901, 902, 903, 904 distribute the force longitudinally along the length of the balloon 910. This force concentration allows the dilation wires 901, 902, 903, 904 to exert a higher stress at their respective points of contact of the pockets 905, 906, 907, 908 with the vessel wall 950 as compared to conventional angioplasty balloons.

The force concentration feature enables dilation of the blood vessel 950 and/or cracking of the calcification rings contained in the blood vessel 950 at a relatively lower inflation pressure as compared to conventional angioplasty balloons. For example, the balloon catheter of FIG. 10 is adapted to burst a calcification ring surrounding a blood vessel at an inflation pressure ranging between about 3 atm to about 30 atm, but preferably in the range of about 4 atm to about 10 atm. The exact inflation pressure is dependent upon numerous factors, including the diameter and geometry of the dilation wires 901, 902, 903, 904 used. Conventional angioplasty balloons may utilize inflation pressures of about 12 atm. A lower inflation pressure is advantageous because it reduces the trauma to the vessel wall 950.

Additionally, the stress exerted by the dilation wires 901, 902, 903, 904 is predictable and controlled, often requiring a single inflation. Because the dilations are predictable, controlled and often isolated to the stenosed segment of the vessel wall 950, restenosis may be limited to occurring only at the points of contact where the dilation wires 901, 902, 903, 904 exert a stress at their respective points of contact with the vessel wall 950. Conventional percutaneous transluminal coronary angioplasty (PTCA) procedures typically involve unpredictable points of rupture along the entire circumference of the blood vessel, which often results in more substantial vessel damage to the entire wall. Additionally, multiple inflations may be required to fracture a calcification ring.

The highest degree of cellular proliferation following balloon angioplasty typically occurs in areas with the greatest degree of vessel disruption. Therefore, the ability to dilate a stenotic region in a more controlled and less disruptive manner at a lower pressure, as described with respect to FIG. 10, may potentially minimize the degree of restenosis. Compared to PTCA procedures, the dilation wires 901, 902, 903, 904 may be capable of providing a controlled dilatation in which the injury to the vessel wall is localized to the dilation site only. The balloon catheter of FIG. 10 may require relatively lower inflation pressures and a relatively smaller number of inflations to produce significant increases in luminal cross section as compared to conventional angioplasty balloons.

Thicknesses of the balloon 140 and the outer layer 130 may vary depending on the particular application of the balloon catheter 100. However, generally speaking, to enhance the stress concentration feature that has been described above, it may be advantageous for the outer layer 130 to be thinner than the balloon layer 140 at the point where the wire contacts the vessel wall.

Figure 11:
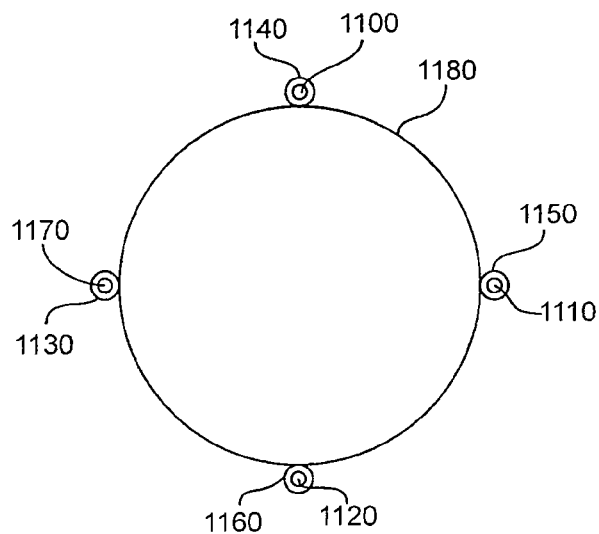
FIG. 11 is a cross-sectional view of a balloon attached to a sheath, the sheath encapsulating a wire therewithin.

The wires have been described as occupying the interior space of a pocketed region. However, other ways of confining the wire are contemplated. For example, each of the wires of the balloon catheter may be encapsulated within a sheath, as shown in FIG. 11. The term "encapsulated" as used herein refers to complete circumscribing of the wire in the radial direction. FIG. 11 shows each of four wires 1100, 1110, 1120, 1130 encapsulated within their respective sheaths 1140, 1150, 1160, 1170. Each of the sheaths 1140, 1150, 1160, 1170 is attached to an outer surface of the balloon 1180, the balloon 1180 shown in its inflated state. In the example of FIG. 11, the sheaths 1140, 1150, 1160, 1170 are spaced 90 degrees apart about the balloon 1180. The sheaths 1140, 1150, 1160, 1170 may be attached to the outer surface of the balloon 1180 in a variety of ways known to one of ordinary skill in the art. As an example, the sheaths 1140, 1150, 1160, 1170 may be fusion bonded to the balloon 1180, as will be discussed in greater detail below.

Figure 12:
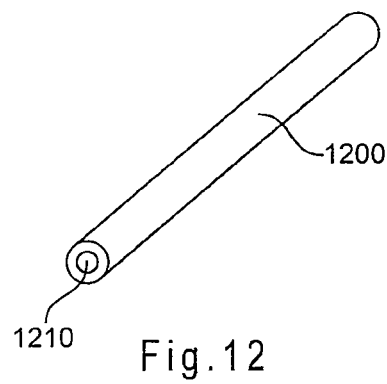
FIG. 12 is a perspective view of a tubular-shaped sheath encapsulating a wire.

FIG. 12 shows one example of a wire-sheath arrangement. A wire 1210 is inserted and encapsulated within a polymeric sheath 1200. The wire 1210 may have a circular cross-section to fit within the polymeric sheath 1200, which may be tubular shaped. The wire 1210 may be inserted into a separate polymeric tube. Alternatively, the polymer may be coated onto the wire 1210 by dip coating, spray coating, extrusion, and other polymer coating techniques. The polymeric sheath 1200 may be formed from any polymeric material known to one of ordinary skill in the art. The polymeric sheath 1200 may be formed from heat-shrink tubing. Preferably, the balloon and the polymeric sheath 1200 are the same materials to facilitate fusion bonding, as will be discussed below, between the balloon and the sheath 1200. Examples of materials that the balloon and sheath 1200 may be formed from include nylon and other polyamides, polyethyleneterepthalate (PET), polyvinylchloride (PVC), polypropylene, polyethylene, polyurethane and high density polyethylene. The wire 1210 may be coated with a non-adhesive coating to minimize bonding between the wire 1210 and the sheath 1200. Examples of a non-adhesive coating include a silicone release or a fluorinated polymer such as PTFE and FEP. This may allow the sheath 1200 to stretch in the axial direction with the balloon without the sheath 1200 significantly pulling on the wire 1210. As a result, the balloon may be free to axially expand without significant restraint.

Figure 13:
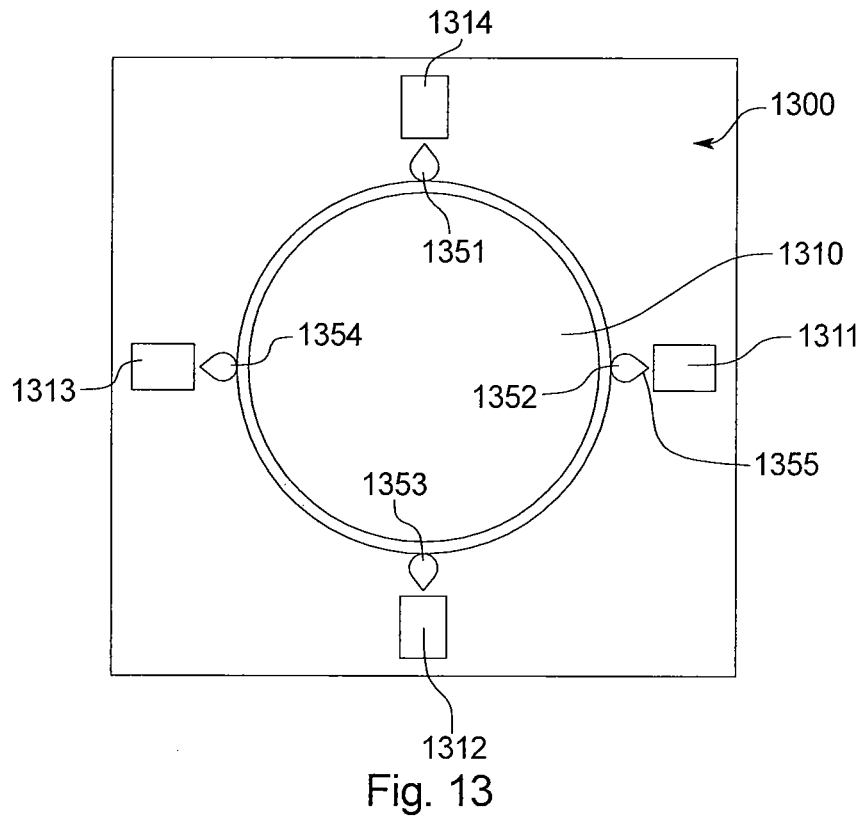
FIG. 13 is a mold assembly for blow molding a balloon with encapsulated wires in a tubular-shaped sheath.

The wire-sheath arrangement may be fusion bonded to the balloon during stretch blow molding of the balloon. The balloon may be formed inside a metal mold from extruded polymer tubing. FIG. 13 shows a cross-section of a metal mold assembly 1300. The mold assembly 1300 includes a cavity 1310 in which a parison is introduced. The parison may be stretched mechanically with a stretch rod. Low pressure air may be introduced into the parison to blow a bubble. The parison is thereafter blow molded into the shape of the balloon as known in the art. Axial stretching of the balloon may also occur to achieve a thinner wall thickness along the neck area of the balloon.

Figure 14:
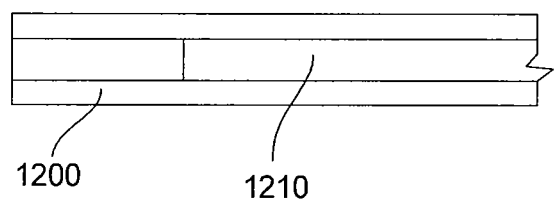
FIG. 14 is a cross-sectional view of one end of a tubular sheath extending past an end of a wire.

FIG. 14 shows the wire-sheath arrangement prior to being fused during the blow molding operation. The part of the tube 1200 that extends past the wire 1210 may be pressed down and fused during blow molding, resulting in the structure of FIG. 15.

Four grooves 1351, 1352, 1353, 1354 are shown adjacent to the cavity 1310. A circular wire with an overlying tubular sheath may be inserted in each of the four grooves 1351, 1352, 1353, 1354. Pressurized air is fed into the cavity 1310 and introduced into one end of the parison to expand it to form the balloon. The other end of the parison is capped off during the air pressurization. The expansion of the parison during the blow molding process fuses the outer surface of the balloon to the polymer sheath (FIG. 12). To maintain the wire and its overlying polymeric sheath in its predetermined position within the grooves 1351-1354 during the blow molding process, magnets 1311, 1312, 1313, 1314 may be placed in the mold adjacent to the grooves 1351, 1352, 1353, 1354. The wires may be any type of a magnetic metal or alloy. As an example, the magnetic alloy may be a series 400 stainless steel. Other methods may be used to fixate the wire-sheath arrangements within their respective grooves 1351-1354 during the blow molding process.

Figure 15:
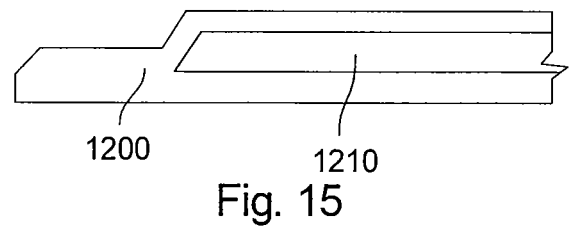
FIG. 15 is a cross-sectional view of one end of a tubular sheath having a beveled end and extending past an end of a wire.

The wire 1210 and sheath 1200 of FIG. 12 preferably extend along the entire length of the working diameter of the balloon 140 (FIG. 1). The sheath 1200 preferably encapsulates the wire 1210 on both ends. FIG. 15 shows that the sheath 1200 may encapsulate the ends of the wire 1210. FIG. 15 shows that the sheath 1200 has a beveled edge to more completely encapsulate the wire 1210. Alternatively, free space may exist for the wire 1200 to move as the sheath 1200 axially stretches and contracts during balloon inflation and deflation.

FIG. 16 shows that the sheath may have an edge to enable cutting of a lesion. FIG. 16 shows a sheath 1620 with an edge 1610 having a wire 1630 disposed within the sheath 1620. The sheath 1610 may be fusion bonded to a surface of the balloon 1660. The edge 1610 may be formed as follows. The grooves 1351, 1352, 1353, 1354 shown in FIG. 13 may be machined such that they converge to a point 1355 at the radially outward side. The tubular-shaped polymer sheath is inserted into the groove around its respective wire. The blow molding process forces some of the material of the sheath to flow into the pointed region of the machined groove, thereby creating the cutting edge 1610 shown in FIG. 16. The cutting edge 1610 may enable tearing or breaking of a lesion from a vessel.

The cutting edge 1610 may be advantageous over other approaches. For example, it is more advantageous than conventional angioplasty because it utilizes the concept of focused force angioplasty to fracture lesions. On the other hand, utilizing the cutting edge 1610 may be more advantageous than metal blades because the cutting edge 1610 may be less likely to injure a vessel wall as compared to the metal blades.

The wall thickness of the sheath 1200 (FIG. 12) depends on several factors. The wall thickness preferably is thin enough to maximize the focusing or transmission of force to the stenosed region of the vessel wall yet sufficiently thick to prevent breakthrough of the wire 1210 through the sheath 1200. Furthermore, a wall thickness that is too thick may render the balloon catheter too longitudinally stiff such that the balloon catheter loses its ability to negotiate through tortuosity of various vessels. However, a cutting edge 1610 as shown in FIG. 16 requires a thicker sheath in order for extra material to flow into the pointed grooves 1351, 1352, 1353, 1354 of the mold assembly 1300. Thus, one of ordinary skill in the art would be able to balance these competing factors in light of the particular application the balloon catheter is to be used for to arrive at the optimal wall thickness of the sheath 1200. In one example, the sheath 1200 may have a wall thickness about equal to or on the same order of magnitude as the balloon 1660 wall thickness.

Although FIG. 12 shows a tubular-shaped sheath 1200, the sheath may possess any shape. Preferably, the sheath has the same shape as the wire such that the sheath can completely circumscribe and encapsulate the wire.

Having encapsulated wires within a sheath offers similar advantages as described above with respect to confining the wires within pockets. The wires are atraumatic as they are shielded from contacting body tissue. The wires also remain oriented in their predetermined position along the balloon catheter, thereby eliminating the risk that the wires inadvertently move relative to each other.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

I claim:

1. A balloon catheter for dilation of a body lumen, comprising:
   a shaft having a distal end and a proximal end;
   a balloon mounted on the distal end of the shaft, the balloon having a distal portion and a proximal portion, the shaft having an inflation lumen extending therethrough in fluid communication with an interior region of the balloon, the balloon thereby being expandable between a deflated state and an inflated state, wherein at least a length of an outer surface of the balloon comprises a working diameter adapted to dilate the body lumen, the length extending between the proximal portion and the distal portion; and
   a plurality of dilation wires, each having a proximal and distal end, extending along a portion of the working diameter of the balloon, each dilation wire being encapsulated in a sheath, each dilation wire being completely circumscribed in a radial direction, and each dilation wire being longitudinally constrained within the sheath, the sheath axially extending past the respective proximal and distal ends of each dilation wire and being pressed down over the respective proximal and distal ends of each dilation wire and being fused to encapsulate each dilation wire;
   wherein the sheath is attached to the outer surface of the balloon and the sheath forms a radially extending cutting edge.

2. The balloon catheter of claim 1, wherein the sheath is fusion bonded to the outer surface of the balloon.

3. The balloon catheter of claim 1, wherein the sheath circumscribes each of the dilation wires along an entire axial length of each of the dilation wires.

4. The balloon catheter of claim 1, wherein the sheath and each of the dilation wires extend along substantially an entire length of the working diameter of the balloon.

5. The balloon catheter of claim 1, wherein the sheath has a tubular shape.

6. The balloon catheter of claim 1, wherein each of the dilation wires has a circular cross-section.

7. The balloon catheter of claim 1, wherein the sheath is polymeric.

8. The balloon catheter of claim 1, wherein the sheath comprises a wall thickness substantially equal to a wall thickness of the balloon.

9. The balloon catheter of claim 1, wherein each of the dilation wires comprises a non-adhesive coating to minimize bonding with the sheath.

10. The balloon catheter of claim 1, wherein the sheath circumscribes each of the dilation wires along an entire axial length of each of the dilation wires, and the sheath is polymeric.

11. The balloon catheter of claim 10, wherein each of the dilation wires has a circular cross-section.

12. A balloon catheter for dilation of a body lumen, comprising: a shaft having a distal end and a proximal end;

a balloon mounted on the distal end of the shaft, the balloon having a distal portion and a proximal portion, the shaft having an inflation lumen extending therethrough in fluid communication with an interior region of the balloon, the balloon thereby being expandable between a deflated state and an inflated state, wherein at least a length of an outer surface of the balloon comprises a working diameter adapted to dilate the body lumen, the length extending between the proximal portion and the distal portion; and a plurality of dilation wires, each having a proximal and distal end, extending along a portion of the working diameter of the balloon, each dilation wire being encapsulated in a sheath, each dilation wire being completely circumscribed in a radial direction, and each dilation wire being longitudinally constrained within the sheath, the sheath axially extending past the respective proximal and distal ends of each dilation wire and being pressed down over the respective proximal and distal ends of each dilation wire and being fused to encapsulate each dilation wire;

wherein the sheath is attached to the outer surface of the balloon and the sheath forms a radially extending cutting edge, and wherein the sheath circumscribes each of the dilation wires along an entire axial length of each of the dilation wires, the sheath and each of the dilation wires extend along substantially an entire length of the working diameter of the balloon, the sheath has a tubular shape and each of the dilation wires has a circular cross section.

13. The balloon catheter of claim 12, wherein the sheath is polymeric, and the sheath is fusion bonded to the outer surface of the balloon.

14. The balloon catheter of claim 13, wherein the sheath comprises a wall thickness substantially equal to a wall thickness of the balloon.

15. The balloon catheter of claim 14, wherein each of the dilation wires comprises a non-adhesive coating to minimize bonding with the sheath.

\* \* \* \* \*